Figure 3:
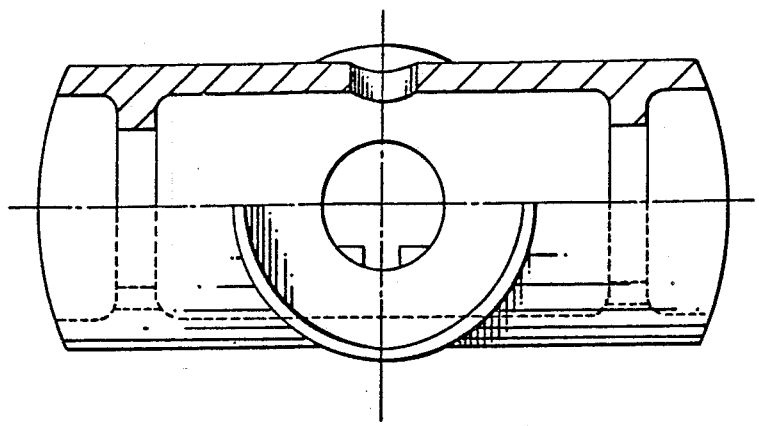

United States Patent [19]

Schlemmer et al.

[11] Patent Number: 4,961,645

[45] Date of Patent: Oct. 9, 1990

[54] ELECTROTHERMAL ATOMIZATION FURNACE

[75] Inventors: Gerhard C. U. Schlemmer, Owingen; Rolf Tamm, Salem; Gunther Roedel, Owingen, all of Fed. Rep. of Germany

[73] Assignee: Bodenseewerk Perkin-Elmer GmbH, Uberlingen, Fed. Rep. of Germany

[21] Appl. No.: 376,324

[22] Filed: Jul. 6, 1989

Related U.S. Application Data

[63] Continuation-in-part of Ser. No. 304,993, Feb. 1, 1989.

[30] Foreign Application Priority Data

Oct. 16, 1987 [DE] Fed. Rep. of Germany ....... 3735013
Feb. 2, 1988 [DE] Fed. Rep. of Germany ....... 3802968

[51] Int. Cl.$^5$ .............................................. G01N 21/74
[52] U.S. Cl. ..................................... 356/312; 356/244
[58] Field of Search ................................. 356/312, 244

[56] References Cited

U.S. PATENT DOCUMENTS 4,726,678 2/1988 Hutsch et al. ...................... 356/312

Primary Examiner—F. L. Evans
Attorney, Agent, or Firm—Edwin T. Grimes; Thomas P. Murphy

[57] ABSTRACT

An electrothermal atomization furnace comprises a tubular furnace body (10) with contact projections (12, 14) arranged on opposite sides and having contractions (56, 58) adjacent to cylindrical contact elements (24, 26) with conical contact surfaces (28, 30). A platform for receiving sample can be placed in the furnace which is only indirectly heated by the furnace. Further, curent-supplying contacts are provided for holding the furnace and through which current is passed transversely through the furnace body. The contacts form a cavity into which inert gas is introduced.

12 Claims, 5 Drawing Sheets

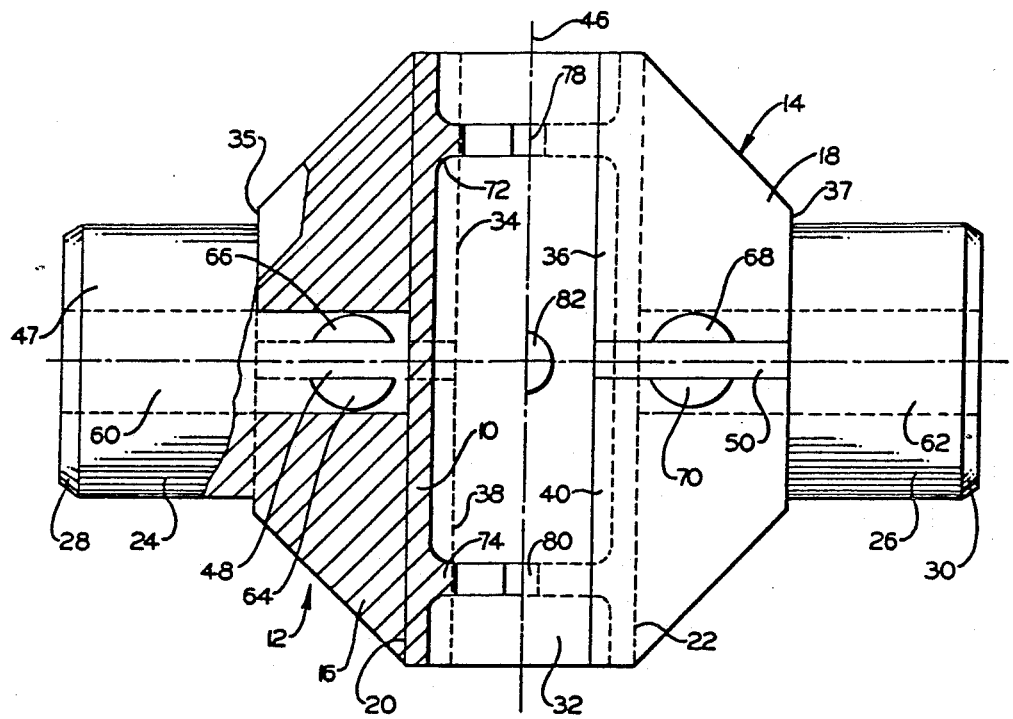
FIG. I
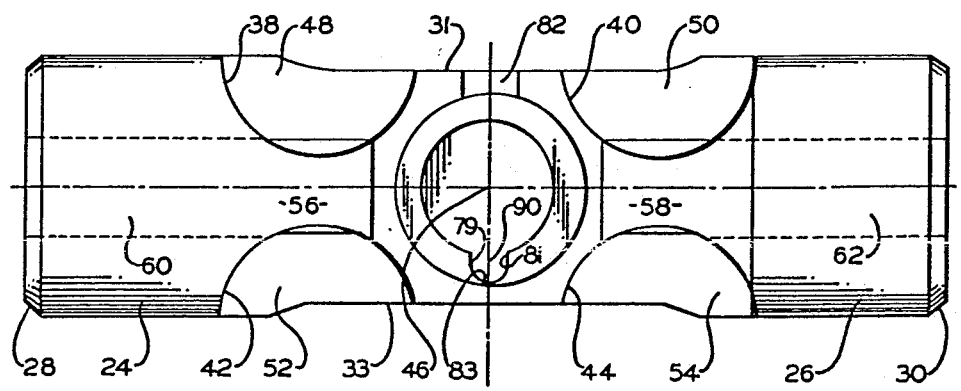
FIG. 2

ELECTROTHERMAL ATOMIZATION FURNACE

This application is a continuation-in-part of copending U.S. patent application Ser. No. 07/304,993 filed Feb. 1, 1989.

BACKGROUND AND SUMMARY OF THE INVENTION

The present invention relates generally to atomic absorption spectroscopy and more particularly to a furnace for electrothermal atomization of samples in atomic absorption spectroscopy.

Electrothermal atomizers, commonly referred to as heated graphite atomizers or graphite furnaces, are utilized in atomic absorption spectrophotometers for rendering the sample to be analyzed into atomic form. Typically, the furnace comprises a tubular graphite member clamped between annular graphite contacts or electrodes engaging its respective ends. A radial aperture in the side wall of the tubular member at the midpoint of its length serves as a sample port accommodating the insertion of the substance to be analyzed into the tubular member.

The contacts, usually mounted in cooling jackets, are pressed into tight engagement with the ends of the tubular furnace member by resilient biasing means or a servomotor. An intense electrical current is passed longitudinally through the tubular member between the contacts and heats the member to the high temperature required to convert the sample to a "cloud of atoms".

A measuring light beam of a line emitting light source which comprises the resonant spectral line of a looked-for element is passed through the annular graphite contacts and the longitudinal bore of the graphite tube. The amount of the looked-for element in the sample can be determined from the absorption of the measuring light beam.

In order to prevent rapid deterioration of the tubular graphite member by oxidation at the high temperatures required for atomization of the analyte, provision is made for enveloping it in a flow of inert protective gas. The graphite tube is surrounded by the inert gas such that oxygen does not come into contact with the graphite tube.

A non-uniform temperature distribution along the graphite tube results when the graphite tube is held at its ends. The graphite tube has a higher temperature at its central area than at the ends where the heat dissipates to the cooler contacts. This non-uniformity of temperature results in the deposition of sample on the cooler ends of the tubular member; the deposit is re-evaporated in subsequent use of the tubular member thereby contaminating the new sample.

A graphite furnace of the type just described is shown in Braun et al., U.S. Pat. No. 4,022,530 which is incorporated herein by reference. In this particular furnace, the contacts are tubular rather than annular. The two contacts extend around the graphite tube along its entire length between the contact surfaces except for a separating gap. An inert gas flow is passed into the graphite tube from both ends. This inert gas flow emerges through a radial bore of the graphite tube in its center. One of the tubular contacts has a radial bore which is aligned with the radial bore of the graphite tube.

In an attempt to achieve a more advantageous temperature distribution along the graphite tube, it has been proposed to pass the heating current transversely through the graphite tube rather than longitudinally. For this purpose, a contact arrangement is described in Woodriff, U.S. Pat. No. 4,407,582 wherein two pairs of interconnected contacts in the form of fork-shaped contact pieces are employed which engage the graphite tube radially on opposite sides. The heating current flows in a circumferential direction through the graphite tube in the area of the ends. The graphite tube is heated in the area of its ends and heat flows from the ends to the center to obtain a more uniform temperature distribution.

In this known contact arrangement, the electrodes engage the hot parts of the graphite tube; consequently, the reproducibility of the contact characteristics is poor. Furthermore, it is difficult to protect the graphite tube from exposure to atmospheric oxygen by means of an inert protective gas flow, resulting in short useful life of the graphite tube.

In Hutsch et al., U.S. Pat. No. 4,726,678 which is incorporated herein by reference and the publication in "Analytical Chemistry" 58 (1986), 1973, a graphite furnace is described in which the tubular furnace body has a rectangular cross-section and contact projections extend transversely to the axis of the furnace body. The furnace body and contact projections are formed as one integral graphite element. The contact is established in a cold zone by planar contact surfaces.

In some embodiments of U.S. Pat. No. 4,726,678, the contact projections between the contact surfaces and furnace body have areas of a reduced cross-section. In one embodiment (FIG. 3), cutouts are provided which extend longitudinally to the furnace body parallel to the furnace axis. These slots or cutouts provide a decrease of the heat flow from the furnace body to the ends of the contact projections and match electrical resistance to the output of the electrical power supply. In another embodiment (FIG. 4), it is stated that the contact projections are provided with multiple apertures and that this configuration is specifically suited for setting predetermined temperature profiles. Current is supplied at certain locations and flows through the furnace body in order to generate Joul's heat. This is similar to the arrangement of U.S. Pat. No. 4,407,582, except that the contacting is displaced to a cooler area.

In the known arrangement, the power is supplied nonuniformly along the tubular furnace body.

It is an object of the present invention to provide a new and improved furnace for electrothermal atomization.

Another object of the invention is to provide an electrothermal atomization furnace which attains uniform temperature distribution along the tubular furnace body.

A further object of the invention is to provide such a furnace which reduces heat dissipation of the tubular furnace body.

A further object of the invention is to provide such a furnace which facilitates effective protection against exposure to atmospheric oxygen.

Other objects will be in part obvious and in part pointed out more in detail hereinafter.

Accordingly, it has been found that the foregoing and related objects are attained in an electrothermal atomization furnace comprising a tubular furnace member adapted for passing a light beam therethrough and a pair of contact projections integrally formed longitudinally along said furnace member on opposite sides thereof so as to uniformly supply current along the furnace member and thereby produce uniform temperature distribution along the furnace member. The contact projections project outwardly from the furnace member with contact surfaces at the distal ends. The contact surfaces are adapted for supporting the furnace member between cooperating current-supplying contact elements. The contact projections have a central axis transverse to the furnace member and each contact projection has a contraction in cross-sectional area about the central axis which is configured and dimensioned to reduce heat dissipation from the furnace member and to increase the relative temperature of the contact projection at the contraction during sample atomization. The contraction is formed by cylindrical recesses on the upper and lower surfaces of the contact projection.

A substantially uniform current supply to the furnace body throughout the length of the furnace body is attained such that the furnace body is heated uniformly. The contractions of the contact projections counteract heat dissipation. On one hand, the cross-sectional area for heat dissipation is reduced. On the other hand, increased Joul's heat is generated in the region of the contraction which acts on the reduced mass such that the contraction assumes an increased temperature which reduces the dissipation of heat from the furnace body to the contact surface. Consequently, a very uniform temperature distribution results at the furnace body with relatively cold contact surfaces.

BRIEF DESCRIPTION OF THE DRAWINGS

FIG. 1 is a plan view of the tubular furnace of the present invention with integral contact projections.

FIG. 2 is a front elevation view of the furnace as viewed in the direction of the furnace axis and the measuring light beam.

FIG. 3 is an associated side elevation view, partially in section, as seen from the left in FIG. 1.

FIG. 4 is a front elevation view, partially in section, of one spectrometer contact member by which the furnace is mounted and supplied with current.

FIG. 5 is the right side view of the contact member of FIG. 4.

FIG. 6 is a front elevation view, partially in section, of the other spectrometer contact member.

FIG. 7 is a plan view of a platform used in the furnace.

FIG. 8 is a side view of the platform of FIG. 7.

FIG. 9 is a front elevation view of the platform of FIG. 7, partially in section.

FIG. 10 is a sectional view illustrating the contact members mounting the furnace in an operational configuration.

DESCRIPTION OF THE PREFERRED EMBODIMENT

Although specific forms of the present invention have been selected for illustration in the drawings, and the following description is drawn in specific terms for the purpose of describing these forms of the invention, the description is not intended to limit the scope of the invention which is defined in the appended claims.

Referring to FIGS. 1 to 3, the electrothermal atomization furnace of the present invention comprises a tubular furnace body 10 made of an electrically conducting material such as graphite which does not affect absorption measurements. Diametrically opposite contact projections 12 and 14 are integral with the furnace body 10. The contact projections 12 and 14 comprise contact ribs 16 and 18, respectively. As seen in FIG. 1, the contact ribs 16 and 18 are each trapezoidal in plan view on the surface of the contact ribs with the longer parallel sides 20, 22, respectively, of the trapezoids extending along the tubular furnace body. Cylindrical contact elements 24, 26, respectively, are integral with the contact ribs 16 and 18 in the region of the shorter parallel sides of the trapezoids. The cylindrical contact elements 24, 26 have conical contact surfaces 28, 30, respectively, at their distal ends.

As seen in FIG. 2, the tubular furnace 10 and contact projections 12 and 14 are formed from a substantially plate-shaped, solid element having a generally octagonal shape in plan view with an upper face 31, a lower face 33, and oppositely disposed side faces 35, 37. The longitudinal bore 32 extends along the furnace axis 46 between the upper and lower faces 31, 33 to form the tubular furnace. The contact elements 24, 26 extend orthogonally from the respective side faces 35, 37 as seen in FIG. 1.

The axis of the contact elements 24, 26 defines, for purposes of explanation, a transverse central plane 47 extending through the contact elements 24, 26 transverse to the furnace axis 46. The contact projection 12 contains a pair of cylindrical recesses 34, 38 in the upper face 31. The recesses 34, 38 extend generally parallel to the furnace axis 46 in spaced-apart disposition from the transverse central plane 47 so as to form a reinforcing rib 48 therebetween. Corresponding cylindrical recesses 42, 43 (not shown) are similarly disposed in the lower face 33 in spaced-apart disposition from the transverse central plane 47 so as to form reinforcing rib 52. In like manner, the contact projection 16 contains cylindrical recesses 36, 40 in the upper surface 31 similarly disposed so as to form a reinforcing rib 50 therebetween and corresponding recesses 44, 45 (not shown) in lower surface 33 forming reinforcing rib 54.

The recesses 34, 38, 42, 43 reduce the cross-sectional area of the contact projection 16 and are arranged to form a constricted or reduced area 56 in the projection 16 which extends substantially uniformly along the length of the contact projection. In like manner, the recesses 36, 40, 44, 45 form a similar constricted or reduced area 58 in the contact projection 18. The constrictions 56, 58 are configured and dimensioned to provide a substantially uniform current supply to the furnace body throughout the length of the furnace body so that the furnace body is uniformly heated. Notably, the constrictions 56, 58 counteract heat dissipation in the furnace body. On one hand, the cross-sectional area for heat conduction is reduced by the constricted areas adjoining the tubular body portion. On the other hand, increased Joul's heat is generated in the region of the constriction which acts on the reduced mass such that the constriction area assumes a higher temperature and therefore reduces the dissipation of heat from the furnace body to the contact surfaces. Consequently, a very uniform temperature distribution is attained at the furnace body with relatively cold contact surfaces.

The adjacent cylindrical contact elements 24, 26 have axial bores 60 and 62, respectively. The bores 60, 62 are intersected on both sides of the reinforcing ribs by the cylindrical recesses 34, 38, 42, 43 and 36, 40, 44, 45, respectively, such that openings 64, 66, 68, 70 (FIG. 1) and corresponding openings on the lower side (not shown) are formed for the escape of inert gas.

Reinforcing rings 72 and 74 are formed in the bore 32 spaced from the ends thereof. The reinforcing rings 72 and 74 support and guide a sample platform 76. For this purpose, the reinforcing rings 72 and 74 have aligned, u-shaped cutouts 78, 80, respectively. A radial bore 82 is provided in the furnace body on its upper side as seen in FIG. 2.

Figure 7:
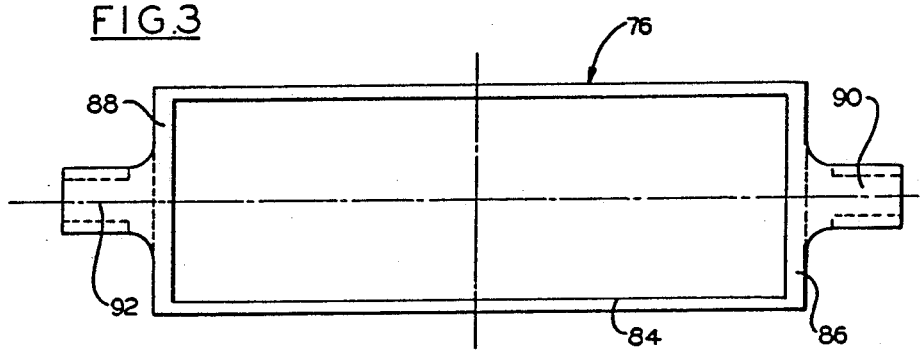
Figure 8:
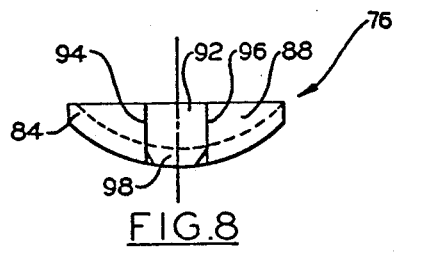
Figure 9:
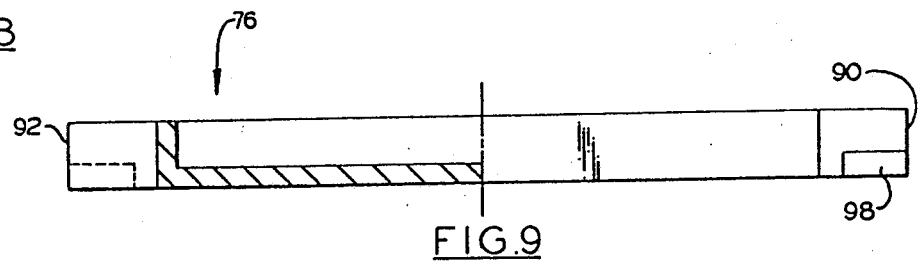
Figure 10:
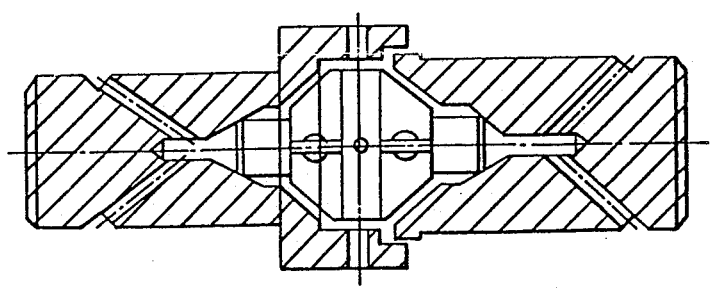

Referring to FIGS. 7–9, the platform 76 forms a rectangular trough 84 with a cylindrical bottom. Projections 90, 92, respectively, are provided on the end faces 86 and 88 of the trough 84 and support the platform 76 in the u-shaped cut-outs 78, 80, respectively. The projections 90, 92 have parallel side faces 94, 96 and base elements 98 of trapezoidal cross-section. The parallel side faces 94, 96 are guided nonrotatably between the opposing planar side faces 79, 81 of the u-shaped cutouts 78 and 80 and base elements 98 are supported on the u-shaped arch portion 83 of the cutouts 78 and 80. Thus, the platform 76 is supported in the furnace only by the projections 90 and 92. Thereby, the platform 76 is heated substantially by indirect radiation of the furnace and there is no current flowing though the platform to generate heat in the platform.

In operation, the tubular furnace just described is supported between two current-supplying contacts 100, 130 and an electric current is passed through these contacts, through the contact elements 24, 26 and contact ribs 16, 18, and transversely through the furnace body 10. The current flows circumferentially around the tubular furnace body 10.

Figure 4:
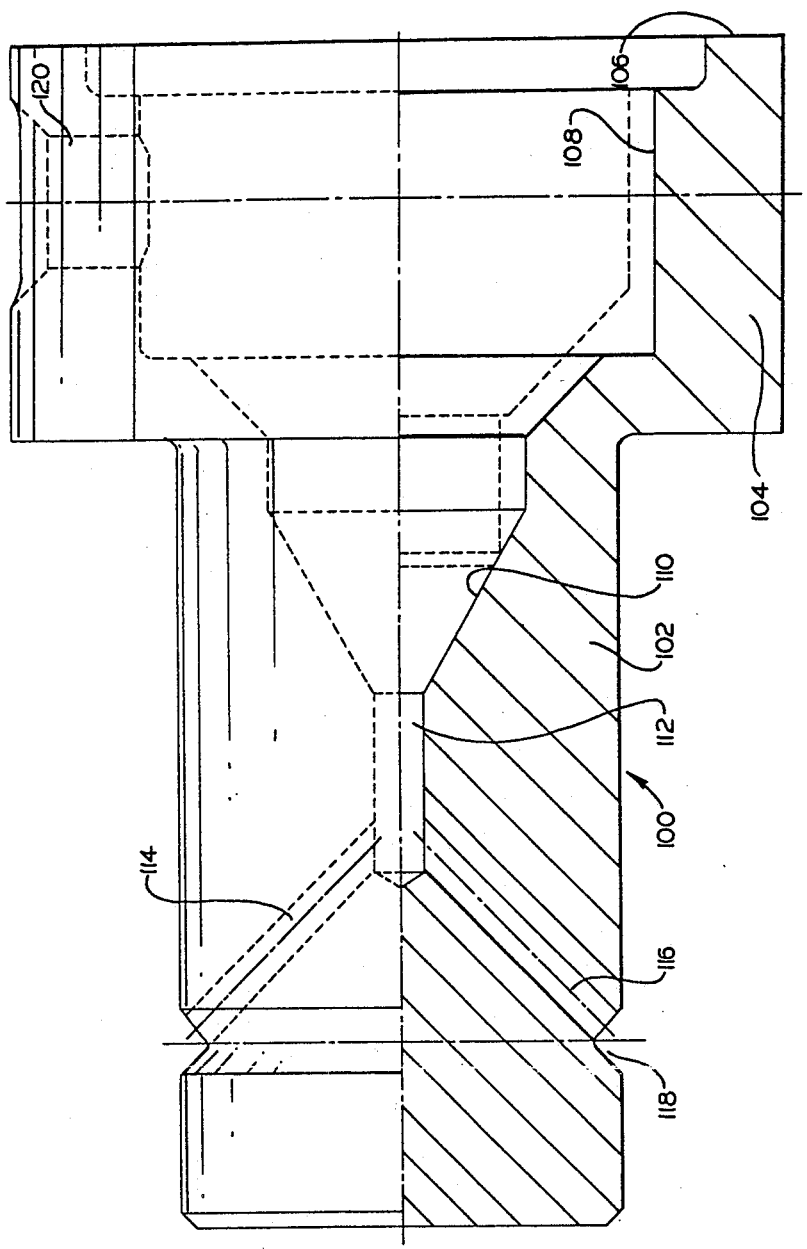
Figure 5:
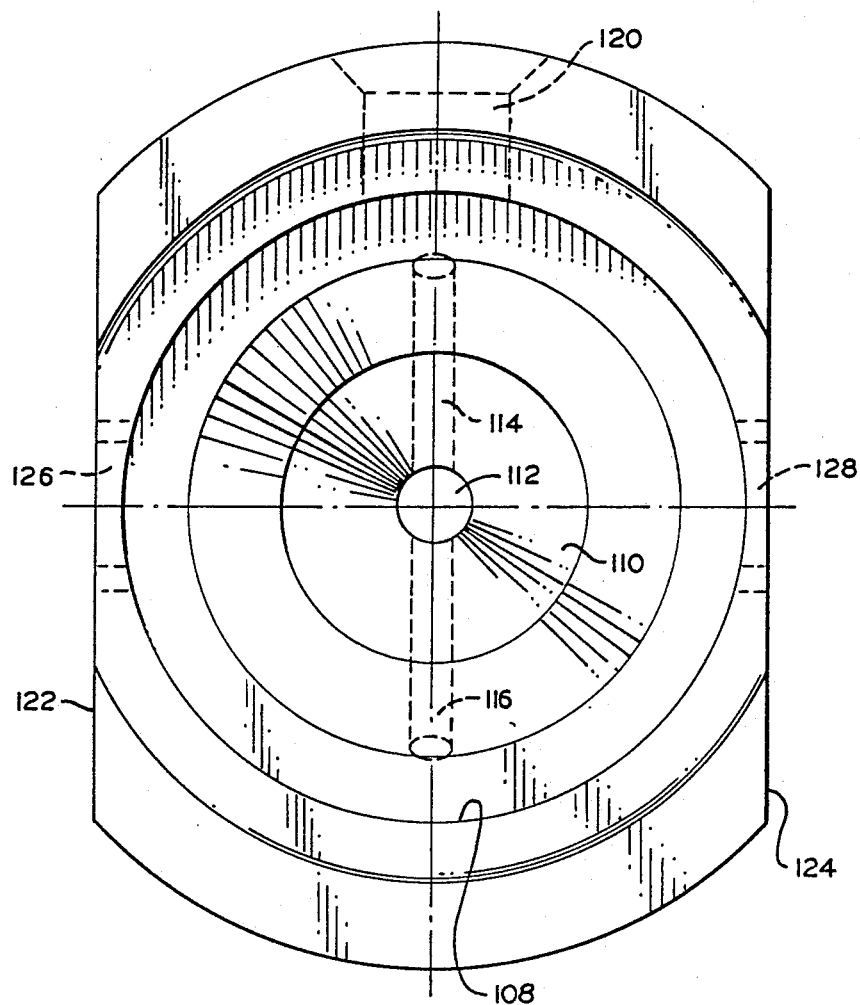

Referring to FIGS. 4 and 5, the current-supplying contact 100 comprises a cylindric shaft 102 and a head portion 104. A recess 108 is formed in the end face 106 of the head portion 104. The recess 108 is shaped to accommodate the furnace with the furnace body 10, contact rib 16 and contact element 24 as indicated in broken line in FIG. 4. A conical contact surface 110 is formed at the bottom of the recess 108 to provide electrical contact with the conical contact surface 28 of the cylindrical contact element 24 of the contact rib 16.

An inert gas conduit 112 opens adjacent to the conical contact surface 110 at the bottom of the recess 108. The inert gas conduit 112 extends along the axis of the shaft 102 and is connected to an outer annular groove 118 by two bores 114 and 116 extending in an oblique direction relative to the shaft axis. The annular groove 118 communicates with an inert gas source when the contact 100 is mounted in the atomic absorption spectrometer.

The head portion 104 has a bore 120 in its outer surface which is aligned with the sample introduction bore 82 of the furnace body 10 when the furnace is inserted within the contact 100. A sample can be introduced into the furnace through the bores 120 and 82, i.e., onto the platform 76 placed in the furnace.

The head portion 104 is flat on two opposite sides to form two parallel, planar surfaces 122, 124. The planar surfaces 122, 124 are parallel to the axis of the bore 120 and contain aligned bores 126, 128, respectively. Thus, the axis of the bores 126, 128 and the axis of the bore 120 are located in mutually perpendicular planes. The axis of the bores 126, 128 coincides with the furnace axis 46 so that the measuring light beam of the atomic absorption spectrometer passes through the bores 126 and 128 and passes along the furnace axis 46 through the bore 32 of the furnace body 10.

Figure 6:
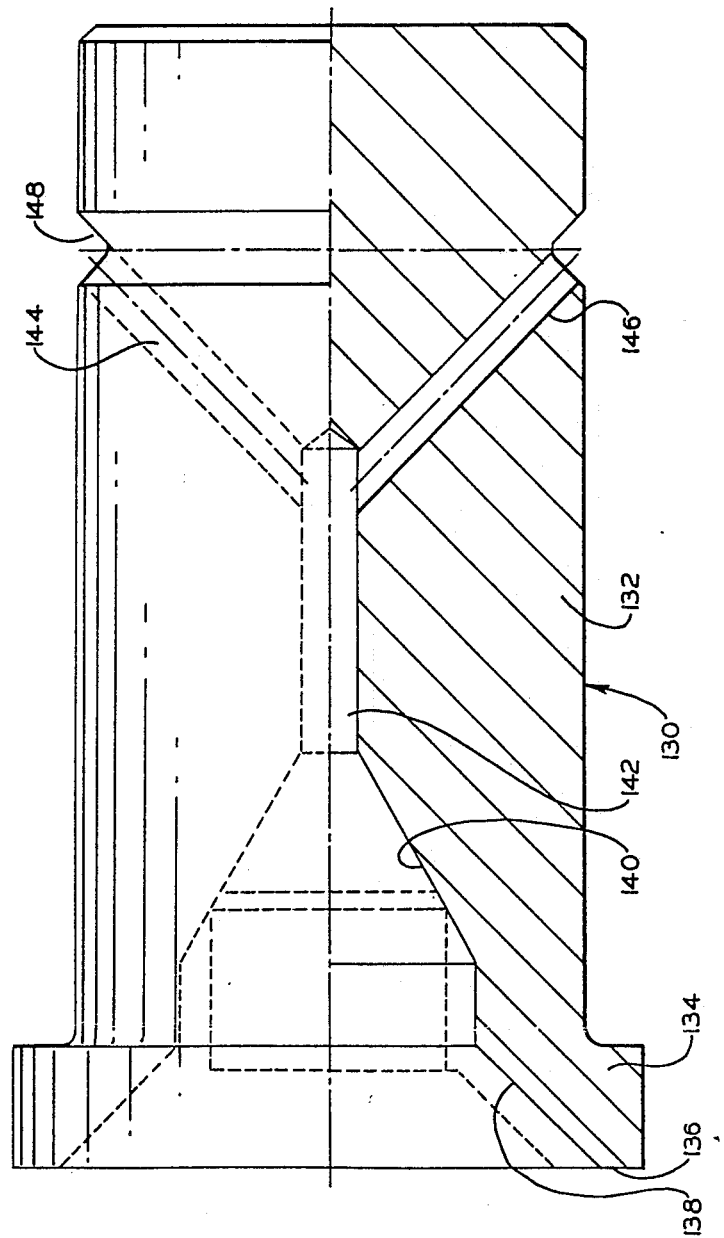

FIG. 6 illustrates the second contact 130 which coacts with the contact 100 to support the furnace. The second contact 130 comprises a shaft 132 and a head portion 134 with an end face 136. In an assembled configuration, the end face 136 is spaced by a short distance from the end face 106 of the first contact 100. Thereby, the two contacts 100 and 130 define a cavity in which the furnace is held. A recess 138 is also formed in the end face 136 which accommodates the contact rib 18 and the contact element 26 of the furnace as indicated in broken line in FIG. 6. The contact 130 has a conical contact surface 140 adjacent to the recess 138 which, in assembly, is engaged by the conical contact surface 30 of the contact element 26.

An inert gas conduit 142 is provided in the shaft 132 adjacent to the conical contact surface 140. The inert gas conduit 142 extends along the axis of the shaft 132 and opens at the inner end of the conical contact surface 140. The inert gas conduit 142 is connected to the annular groove 148 of the shaft 132 by oblique bores 144, 146. Similarly to annular groove 118, the annular groove 148 is connected to an inert gas source when the contact 130 is assembled in the atomic absorption spectrometer.

In assembly, the furnace is supported between the contacts 100, 130 and the bores 60 and 62 of the furnace are connected to the inert gas conduits 112, 142, respectively, of the contacts 100, 130. Inert gas emerges from the inert gas conduits 112, 142 and flows through the bores 60, 62 and the openings 64, 66, 68, 70 and the corresponding openings on the other side to the cavity formed between the contacts 100 and 130 and flows around the furnace to surround the furnace with inert gas. Accordingly, the furnace is protected from exposure to air and thus the burning of the furnace at high temperature is prevented.

As can be seen, an improved electrothermal atomization furnace has been described which provides uniform temperature distribution along the furnace body with reduced heat dissipation. In addition, there is effective protection against exposure to atmospheric oxygen.

As will be apparent to persons skilled in the art, various modifications and adaptations of the structure above described will become readily apparent without departure from the spirit and scope of the invention, the scope of which is defined in the appended claims.

What is claimed is:

1. An electrothermal atomization furnace assembly for atomizing sample for analysis by atomic absorption spectrophotometry comprising
   a tubular furnace member adapted for passing a light beam therethrough and having a longitudinal bore and central furnace axis,
   contact projections integrally formed longitudinally along said furnace member on opposite sides thereof so as to provide uniform current supply to the furnace member throughout the length thereof, said contact projections projecting outwardly from said furnace member and having distal ends,
   contact surfaces on the distal ends of said contact projections adapted for supporting the furnace member between cooperating current-supplying contacts, and
   said contact projections having a central axis transverse to said furnace member, each said contact projection having a contraction in cross-sectional area about said central axis between said distal end and said furnace member, said contraction being dimensioned and configured to reduce heat dissipation from said furnace member and to increase the relative temperature of said contraction during sample atomization.

2. The device of claim 1 wherein each said contraction comprises a portion of said contact projection being progressively smaller in cross-sectional area along said central axis toward said furnace member and substantially uniform longitudinally along said furnace member.

3. The device of claim 1 wherein each said contact projection has oppositely disposed upper and lower surfaces with said contractions being formed by pairs of spaced-apart cylindrical recesses oppositely disposed in said upper and lower surfaces and extending parallel to said longitudinal bore of said furnace member.

4. The device of claim 1 wherein said contact projections comprise two oppositely disposed longitudinal contact ribs forming said contractions and cylindrical contact elements at said distal ends integral with said contact ribs.

5. The device of claim 4 wherein said contact elements have conically tapered distal ends forming said contact surfaces.

6. The device of claim 4 wherein
each said contact rib has upper and lower opposing surfaces of trapezoidal shape with a long parallel side of the trapezoid being adjacent the furnace member and said contact element extending from a shorter parallel side of the trapezoid and
said upper and lower surfaces contain cylindrical recesses parallel to said furnace member and forming said contraction.

7. The device of claim 6 which comprises central reinforcing ribs on each side of said contact ribs extending perpendicular to said furnace axis and being interconnected to said furnace member and said contact ribs.

8. The device of claim 7 wherein gas supply bores extend transverse to said furnace member through said cylindrical contact elements and contact ribs and intersect said cylindrical recesses on both sides of said reinforcing ribs so as to form openings for inert gas to emerge and flow over said furnace.

9. The device of claim 4 wherein said furnace member comprises has a pair of reinforcing rings integrally formed within said longitudinal bore in spaced disposition from the ends thereof.

10. The device of claim 9 which comprises
said reinforcing rings having aligned u-shaped recesses and
a substantially rectangular sample platform having support projections extending from each end, said support projections being received within said recesses of said rings to mount said platform, said support projections being the only areas of contact with said furnace member so that said sample platform is heated substantially by radiation.

11. The device of claim 5 which comprises
a current-supplying contact assembly means for supporting said furnace member and conducting current through said contact surfaces,
said contact assembly means having first and second cooperating contact members configured to form a cavity therebetween and coacting to mount said furnace member within said cavity, and
said first and second contact members having opposed facing first and second conical contact surfaces each engaging a said respective conically tapered distal end of said cylindrical contact elements to mount said furnace member within said cavity.

12. The device of claim 11 wherein
said first contact member has a head portion with an end face and a first recess in said end face, said first recess being configured to form a portion of said cavity and receive a portion of said furnace member therein, said first recess having an inner surface forming said first conical contact surface,
said first contact member having first conduit means for conducting inert gas to said first recess,
said second contact member has a head portion with an end face and a second recess in said end face, said second recess being configured to form a portion of said cavity and receive a portion of said furnace member therein, said second recess having an inner surface forming said second conical contact surface, and
said second contact member having second conduit means for conducting inert gas to said second recess.

* * * * *